US00PP22179P2

(12) United States Plant Patent
Kobayashi

(10) Patent No.: US PP22,179 P2
(45) Date of Patent: Oct. 4, 2011

(54) POINSETTIA PLANT NAMED 'PER1232'

(50) Latin Name: ***Euphorbia pulcherrima* Willd.**
Varietal Denomination: PER1232

(75) Inventor: Ruth Kobayashi, Carlsbad, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 12/800,182

(22) Filed: May 10, 2010

(51) Int. Cl.
*A01H 5/00* (2006.01)

(52) U.S. Cl. ..... Plt./307

(58) Field of Classification Search ..... Plt./307
See application file for complete search history.

*Primary Examiner* — June Hwu
(74) *Attorney, Agent, or Firm* — C. A. Whealy

(57) ABSTRACT

A new and distinct cultivar of Poinsettia plant named 'PER1232', characterized by its uniform, upright and mounded plant habit; moderately vigorous growth habit; freely branching habit; dark green-colored leaves; mid-season flowering response; under natural season conditions, plants flower in about nine weeks in Southern California; large inflorescences with upright dark red-colored flower bracts; and good post-production longevity.

1 Drawing Sheet

Botanical designation: *Euphorbia pulcherrima* Willd.
Cultivar denomination: 'PER1232'.

BACKGROUND OF THE INVENTION

The present invention relates to a new and distinct cultivar of Poinsettia plant, botanically known as *Euphorbia pulcherrima* Willd., and hereinafter referred to by the name 'PER1232'.

The new Poinsettia plant is a product of a planned breeding program conducted by the Inventor in Encinitas, Calif. The objective of the breeding program is to create new uniform Poinsettia plants having large inflorescences with red-colored flower bracts, mid-season flowering habit and excellent post-production longevity.

The new Poinsettia plant originated from a cross-pollination made by the Inventor in December, 2004 of a proprietary selection of *Euphorbia pulcherrima* Willd. identified as code number 04-4847, not patented, as the female, or seed, parent, with *Euphorbia pulcherrima* Willd. 'PER1090', disclosed in U.S. Plant Pat. No. 18,203, as the male, or pollen, parent. The new Poinsettia plant was discovered and selected by the Inventor as a flowering plant within the progeny of the stated cross-pollination in a controlled greenhouse environment in Encinitas, Calif. in December, 2005.

Asexual reproduction of the new Poinsettia plant by terminal vegetative cuttings in a controlled greenhouse environment in Encinitas, Calif. since July, 2006, has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER1232'. These characteristics in combination distinguish 'PER1232' as a new and distinct cultivar of Poinsettia plant:

1. Uniform, upright and mounded plant habit.
2. Moderately vigorous growth habit.
3. Freely branching habit.
4. Dark green-colored leaves.
5. Mid-season flowering response; under natural season conditions, plants flower in about nine weeks in Southern California.
6. Large inflorescences with upright dark red-colored flower bracts.
7. Good post-production longevity.

In side-by-side comparisons conducted in Encinitas, Calif., plants of the new Poinsettia differed primarily from plants of the female parent selection in flower bract color as plants of the female parent selection had lighter red-colored flower bracts.

In side-by-side comparisons conducted in Encinitas, Calif., plants of the new Poinsettia differed from plants of the male parent, 'PER1090', in the following characteristics:

1. Plants of the new Poinsettia were not as vigorous as plants of 'PER1090'.
2. Flower bracts of plants of the new Poinsettia were darker red in color than flower bracts of plants of 'PER1090'.
3. Plants of the new Poinsettia flowered five days later than plants of 'PER1090' when grown under natural season conditions.

Plants of the new Poinsettia can be compared to plants of the *Euphorbia pulcherrima* Willd. 'Peterstar', disclosed in U.S. Plant Pat. No. 8,259. In side-by-side comparisons conducted in Encinitas, Calif., plants of the new Poinsettia differed from plants of 'Peterstar' in the following characteristics:

1. Leaves of plants of the new Poinsettia were darker green in color than leaves of plants of 'Peterstar'.
2. Flower bracts of plants of the new Poinsettia were darker red in color than flower bracts of plants of 'Peterstar'.

3. Plants of the new Poinsettia flowered about six days later than plants of 'Peterstar' when grown under natural season conditions.

Plants of the new Poinsettia can also be compared to plants of the *Euphorbia pulcherrima* Willd. '490', disclosed in U.S. Plant Pat. No. 7,825. In side-by-side comparisons conducted in Encinitas, Calif., plants of the new Poinsettia differed primarily from plants of '490' in time to flower as plants of the new Poinsettia flowered about 13 days later than plants of '490' when grown under natural season conditions.

BRIEF DESCRIPTION OF THE PHOTOGRAPHS

The accompanying photographs illustrate the overall appearance of the new Poinsettia plant. These photographs show the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1232' grown in a container.

The photograph at the top of the sheet is a close-up view of a typical inflorescence of 'PER1232'.

DETAILED BOTANICAL DESCRIPTION

Plants used in the aforementioned photographs and in the following description describe plants grown in during the autumn and early winter in 15-cm containers in a polyethylene-covered greenhouse in Encinitas, Calif. and under natural season conditions and cultural practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Plants were pinched one time and were 19 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1232'.

Parentage:

*Female, or seed, parent.*—Proprietary selection of *Euphorbia pulcherrima* Willd. identified as code number 04-4847, not patented.

*Male, or pollen, parent.*—*Euphorbia pulcherrima* Willd. 'PER1090', disclosed in U.S. Plant Pat. No. 18,203.

Propagation:

*Type.*—Terminal vegetative cuttings.

*Time to initiate roots.*—About seven to ten days at 21° C.

*Time to produce a rooted young plant.*—About four weeks at 21° C.

*Root description.*—Fibrous; white in color.

Plant description:

*Plant habit and form.*—Uniform, upright and mounded plant habit; narrow inverted triangle; large inflorescences positioned above the foliar plane; moderately vigorous growth habit.

*Plant height.*—About 32 cm.

*Plant diameter or spread.*—About 45 cm.

*Lateral branch description.*—Quantity: Freely branching habit, about eight lateral branches develop after pinching. Length: About 24 cm. Diameter: About 6 mm. Internode length: About 1.8 cm. Strength: Strong. Texture: Smooth, glabrous. Color: Close to 146B.

*Foliage description.*—Arrangement: Alternate, simple. Aspect: Flat. Length: About 14.4 cm. Width: About 7.6 cm. Shape: Elliptical. Apex: Acute. Base: Obtuse. Margin: Entire. Venation pattern: Pinnate, arcuate. Texture, upper surface: Smooth, glabrous. Texture, lower surface: Pubescent. Color: Developing leaves, upper surface: Close to 147A. Developing leaves, lower surface: Close to N137A. Fully expanded leaves, upper surface: Darker than 147A; venation, close to 147C. Fully expanded leaves, lower surface: Close to N137A; midvein, close to 183C and lateral veins, close to 197B. Petiole: Length: About 5.6 cm. Diameter: About 3 mm. Texture, upper and lower surfaces: Smooth, glabrous. Color, upper surface: Close to 187B. Color, lower surface: Close to 187C.

Inflorescence description:

*Inflorescence type and habit.*—Inflorescences are compound corymbs of cyathia with colored flower bracts subtending the cyathia; inflorescences positioned above the foliar plane.

*Quantity of inflorescence.*—One inflorescence develops per lateral branch.

*Fragrance.*—Not detected.

*Natural flowering season.*—Plants typically flower during the autumn and winter in Southern California; inflorescence initiation and development can also be induced under artificial long nyctoperiod/short photoperiod conditions; mid-season flowering habit, plants flower about nine weeks when grown under natural season conditions in Southern California.

*Post-production longevity.*—Good post-production longevity; plants of the new Poinsettia maintain good substance and flower bract color for about four weeks under interior conditions; inflorescences persistent.

*Inflorescence size.*—Diameter: About 36 cm. Height (depth): About 9 cm.

*Flower bracts.*—Quantity per inflorescence: About 20. Length, largest bracts: About 15.2 cm. Width, largest bracts: About 10.6 cm. Shape: Lanceolate to elliptical. Apex: Acute. Base: Obtuse. Margin: Entire. Texture, upper and lower surfaces: Smooth, glabrous. Aspect: Outer flower bracts mostly horizontal; inner flower bracts upright. Venation pattern: Pinnate, arcuate. Color: Developing or transitional bracts, upper surface: Close to N34A. Developing or transitional bracts, lower surface: Towards the apex and margins, close to N34C; centers, close to 146D. Fully expanded bracts, upper surface: Close to 46A; venation, close to 46A; color does not fade with development. Fully expanded bracts, lower surface: Close to 47A; venation, close to 47A; color does not fade with development. Bract petiole: Length: About 4 cm. Diameter: About 3 mm. Texture, upper and lower surfaces: Slightly pubescent. Color, upper and lower surfaces: Close to 183B.

*Cyathia.*—Quantity per corymb: About twelve. Length: About 1 cm. Width: About 6 mm. Shape: Ovoid. Color, immature: Close to 144A. Color, mature: Close to 144B to 144C. Nectaries: Quantity per cyathium:

One. Length: About 6 mm. Width: About 3 mm. Shape: Elliptical. Color: Close to 14A.

*Peduncles.*—Length: About 2.5 mm. Diameter: About 2 mm. Strength: Strong. Aspect: Mostly upright. Texture: Smooth, glabrous. Color: Close to 144C.

*Reproductive organs.*—Stamens: Quantity per cyathium: About six to ten. Filament length: About 3 mm. Filament color: Close to 185B. Anther shape: Oval; bi-lobed. Anther length: About 1 mm. Anther color: Close to 187A. Amount of pollen: Scarce. Pollen color: Close to 15A. Pistils: Plants of the new Poinsettia do not develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15.5° C. to about 30° C.

It is claimed:

1. A new and distinct Poinsettia plant named 'PER1232' as illustrated and described.

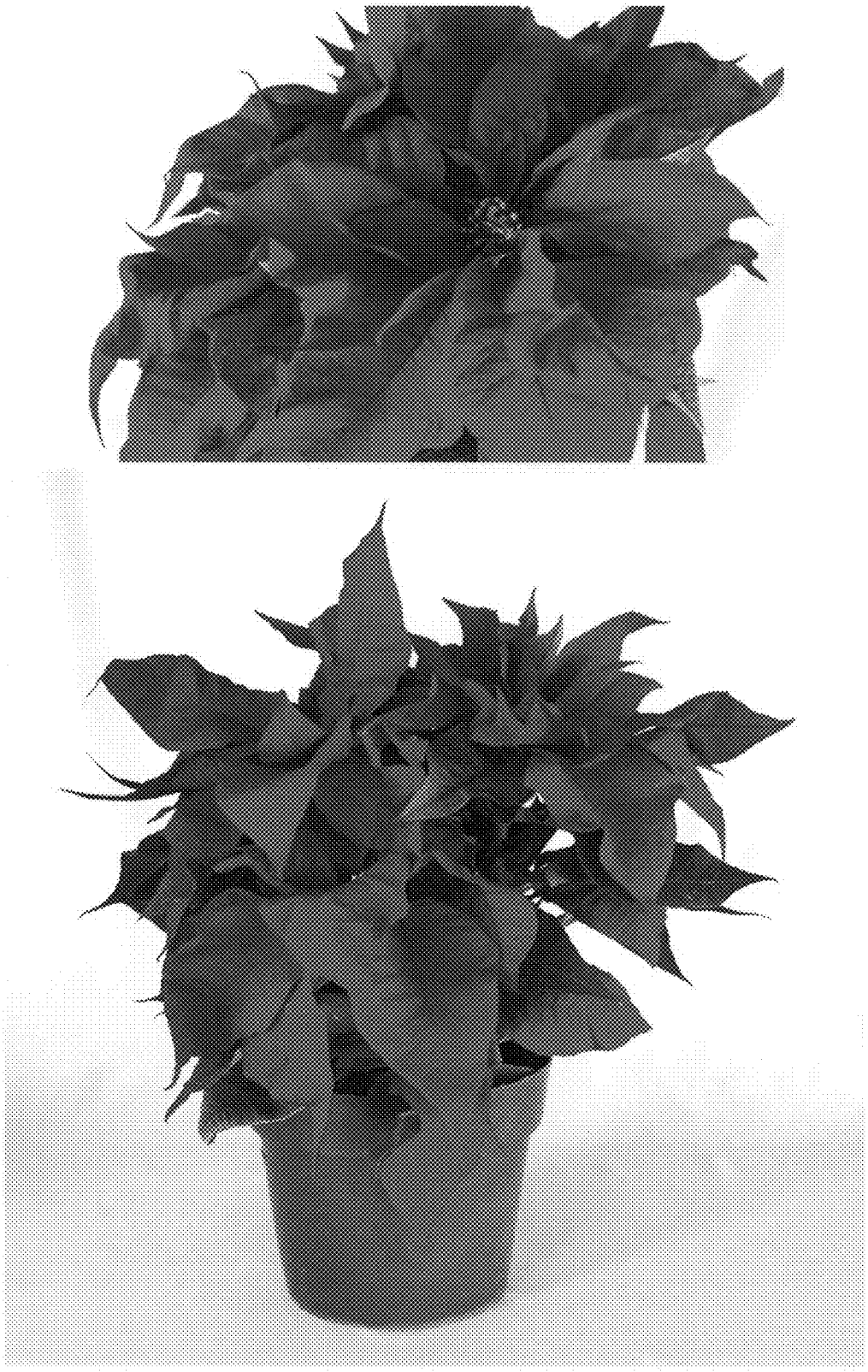

* * * * *